United States Patent [19]

Cohen et al.

[11] Patent Number: 4,750,619

[45] Date of Patent: Jun. 14, 1988

[54] PACKAGE WITH TRAY FOR SECURING AND PRESENTING A STERILE PROSTHETIC IMPLANT ELEMENT

[75] Inventors: Herbert Cohen, W. Milford, N.J.; Harvey L. Goodman, Monroe, N.Y.

[73] Assignee: Osteonics Corp., Allendale, N.J.

[21] Appl. No.: 83,485

[22] Filed: Aug. 10, 1987

[51] Int. Cl.$^4$ ............................................. A61B 17/06
[52] U.S. Cl. .................................. 206/438; 206/363; 206/828; 206/45.14
[58] Field of Search ............... 206/438, 363, 364, 365, 206/366, 367, 368, 369, 370, 45.14, 45.15, 828

[56] References Cited

U.S. PATENT DOCUMENTS

| | | | |
|---|---|---|---|
| 2,851,035 | 9/1958 | Perry et al. | 206/438 |
| 4,101,031 | 7/1978 | Cromie | 206/438 |
| 4,545,783 | 10/1985 | Vaughan | 206/438 |
| 4,697,703 | 10/1987 | Will | 206/438 |

Primary Examiner—Joseph Man-Fu Moy
Attorney, Agent, or Firm—Samuelson & Jacob

[57] ABSTRACT

A package for a sterile prosthetic implant element includes a tray received within a receptacle and having hinged leaves such that upon placement of the tray within the receptacle and folding the leaves of the tray, the prosthetic implant element is confined within a defined envelope wherein the element is protected against damage during handling resulting from shipping and storage and is sealed against contamination, and upon withdrawal from the receptacle, the tray is opened to present the sterile element directly to the surgeon for implant, without the necessity for additional handling.

12 Claims, 3 Drawing Sheets

PACKAGE WITH TRAY FOR SECURING AND PRESENTING A STERILE PROSTHETIC IMPLANT ELEMENT

The present invention relates generally to the packaging and handling of surgical implants, and pertains, more specifically, to packages for sterile prosthetic implant elements, which packages facilitate handling, such as during shipment and storage, and the presentation of a sterile prosthetic implant element for implant, without the necessity for excessive handling of the element itself.

The widespread use of prosthetic implant devices has led to an increase in the production and distribution of such devices and a concomitant demand for more effective techniques for handling these devices, during shipment and storage, as well as during the actual implant procedure. Thus, the various elements of prosthetic implants are manufactured with extreme care to provide precise control over the dimensions and finish of each element and it becomes imperative to protect the completed element against any damage which could alter the ability of the element to function as desired. In addition, the elements of a prosthetic implant device must be packaged and maintained under sterile conditions and then delivered, sterile, to the surgeon for implant, all without risk of contamination. The present invention provides for the packaging of a prosthetic implant element so as to enable shipping and storage with a minimum risk of damage, while maintaining the desired degree of cleanliness right up to the implant procedure. Accordingly, the invention provides a sturdy, integrated packaging system which exhibits several objects and advantages, some of which may be summarized as follows: Protection of a prosthetic implant element against damage during shipment, handling and storage; protection against contamination so as to maintain a packaged prosthetic implant element sterile, even up to the point where the element is presented to a surgeon for implant; ease of packaging, with a high degree of package integrity, while maintaining simplicity of design and construction for economical, widespread use; ease of unpacking for use so as to facilitate delivery and presentation of the packaged prosthetic implant element for implant; economical construction for providing maximum performance at a reasonable cost, while rendering the packaging itself readily expendable; and ready manufacture and use in connection with a wide variety of prosthetic implant elements, in large numbers of uniformly high quality.

The above objects and advantages, as well as further objects and advantages, are attained by the present invention which may be described briefly as providing, in a package for a sterile prosthetic implant element, the package including a walled receptacle and a sealing cover for encasing the prosthetic implant element within a sterile enclosure, a tray for securing the prosthetic implant element within the enclosure for storage and shipment and facilitating removal from the enclosure and presentation of the prosthetic implant element directly to a surgeon during an implant procedure, the tray comprising: a platform extending longitudinally between opposite ends and laterally between opposite sides; a leaf hinged to the platform at each of the opposite ends of the platform, each leaf having longitudinally opposite ends and laterally opposite sides, and being movable between an open position wherein the leaves project essentially longitudinally outwardly from the ends of the platform, and a folded position wherein the leaves project essentially altitudinally from the ends of the platform; and confining means associated with the platform and with the leaves, the confining means arranged such that upon placement of the leaves in the folded position the tray is receivable within the receptacle, with the platform, the leaves and the confining means establishing a defined envelope within which the prosthetic implant element is confined when packaged for storage and shipment, and upon removal of the tray from the receptacle and movement of the leaves to the open position, the prosthetic implant element is presented directly to the surgeon for implant.

The invention will be understood more fully, while still further objects and advantages will become apparent, in the following detailed description of a preferred embodiment of the invention illustrated in the accompanying drawing, in which.

Figure 1:
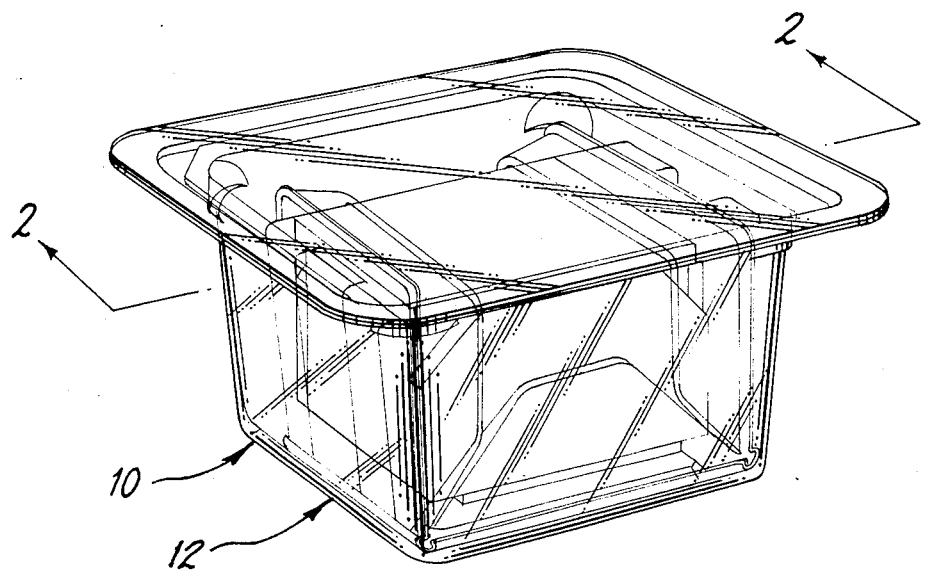
FIG. 1 is a perspective view of a closed package constructed in accordance with the present invention.
Figure 2:
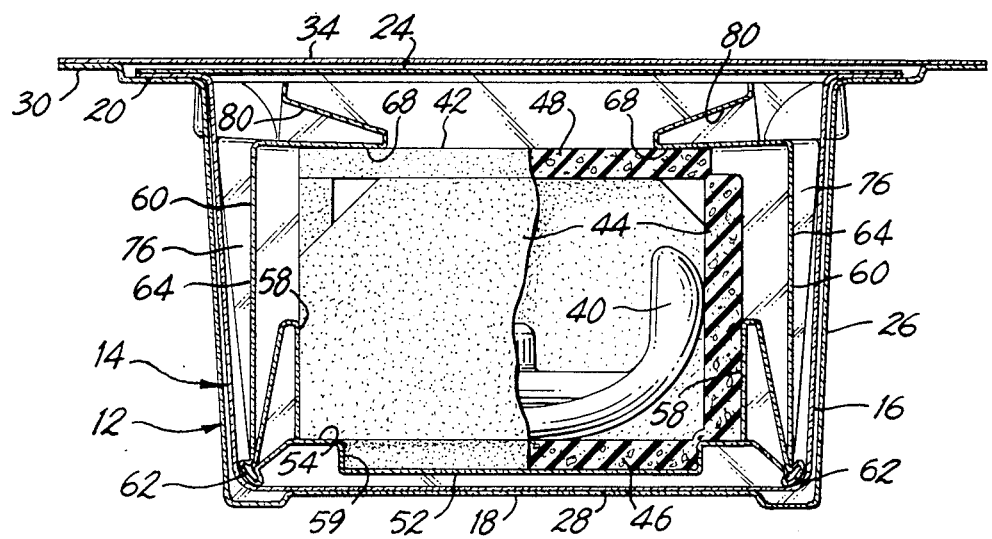
FIG. 2 is an elevational cross-sectional view taken along line 2—2 of FIG. 1.
Figure 3:
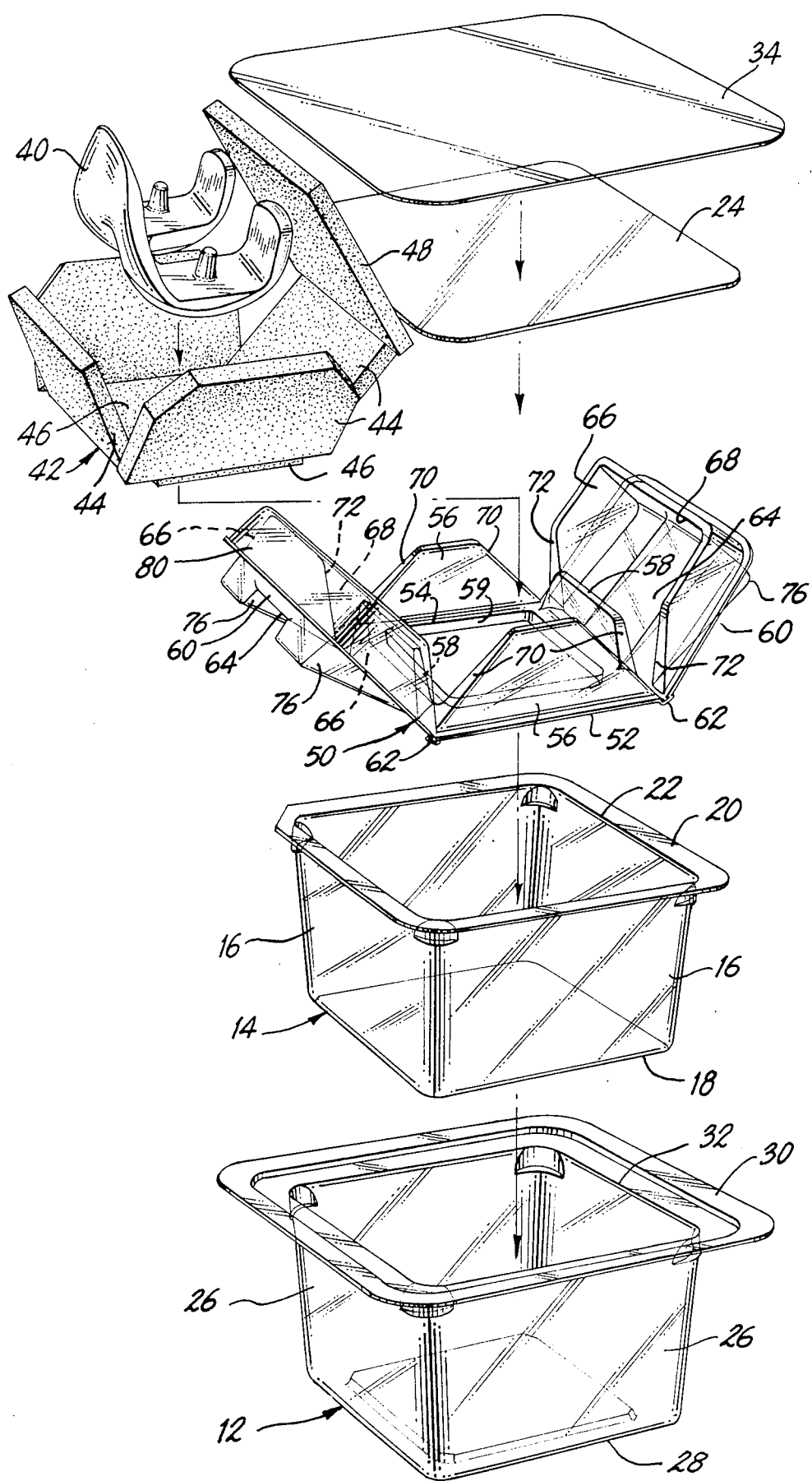
FIG. 3 is an exploded perspective view of the package of FIG. 1.

Referring now to the drawing, and especially to FIGS. 1 through 3 thereof, a package constructed in accordance with the invention is illustrated generally at 10 and is seen to include an outer receptacle 12, and an inner receptacle 14 received within the outer receptacle 12, when the package 10 is closed, as depicted in FIGS. 1 and 2. Inner receptacle 14 has side walls 16 which extend upwardly, in an altitudinal direction, from a closed bottom 18 to a lip 20 which extends laterally outwardly around an open top 22. When package 10 is closed, a first cover 24 is placed over the top 22 of inner receptacle 14 and is secured along lip 20 to seal the interior of the inner receptacle 14. In a like manner, outer receptacle 12 has side walls 26 which extend upwardly, in an altitudinal direction, from a closed bottom 28 to a lip 30 extending laterally outwardly around an open top 32. When package 10 is closed, a second cover 34 is placed over the top 32 of outer receptacle 12 and is secured along lip 30 to seal the interior of the outer receptacle 12. Preferably, the receptacles 12 and 14 are constructed of a thermoplastic synthetic resin material, vacuum formed into the illustrated configuration. In the illustrated embodiment, the material is transparent. Covers 24 and 34 also are formed of a thermoplastic synthetic resin material and are secured into place by heat sealing along the respective lips 20 and 30. When package 10 is closed and sealed, as illustrated in FIGS. 1 and 2, inner receptacle 14 is closed and sealed by cover 34 and is then nested within outer receptacle 12 which, in turn, is closed and sealed by cover 24. The contents of the inner receptacle 14 are thus double-sealed against contamination, for purposes which will be explained in greater detail below.

A prosthetic implant element 40 is packaged within package 10. In this instance, the prosthetic implant element 40 is in the form of the femoral component of a prosthetic knee implant; however, it is to be understood that other elements may be packaged in a similar manner. Element 40 first is placed in a box-like casing 42, preferably constructed of a pad of resilient material, such as a foamed synthetic resin material, scored to define side walls 44, a bottom 46 and a top 48, all establishing the cushioned casing 42 which serves as a protective lining around the envelope within which element 40 is to be contained. Casing 42 then is closed to encase element 40 within the protective envelope provided by the cushioned casing 42 and the casing 42 is seated upon a tray 50. Tray 50 includes a platform 52 extending laterally between opposite sides and longitudinally between opposite ends, the platform 52 having a base 54 upon which casing 42 is received. A pair of opposite side walls 56 are integral with the platform 52, one side wall 56 extending altitudinally upwardly from each side of the platform 52. A pair of opposite end walls 58 are integral with the platform 52, one end wall 58 extending altitudinally upwardly from each end of the platform 52. Upon placement of the casing 42 upon the base 54 of platform 52, the casing 42 is nested securely within the confines of the side walls 56 and the end walls 58. The bottom 46 of the casing 42 is received within a complementary well 59 in the base 54 of platform 52 of tray 50 to assist in locating the casing 42 in proper registry with the tray 50.

A leaf 60 is hinged to platform 52 at each end of the platform 52 by means of an integral hinge 62, enabling each leaf 60 to be moved selectively between an extended, or open position, as illustrated in FIG. 3, and a folded position, as seen in FIG. 2. Each leaf 60 includes a web 64 which carries laterally opposite side walls 66 integral therewith, each side wall 66 extending altitudinally relative to web 64 at each side of the leaf 60. An end wall 68 is integral with each web 64 and extends altitudinally relative to the web 64 at the end of the web 64 longitudinally opposite the corresponding hinge 62. Once the casing 42, with the element 40 encased therein, a seated upon the platform 52, leaves 60 are moved into the folded position so that the side walls 66 of the leaves 60 are juxtaposed with the side walls 56 of the platform 52, the angled portions 70 and 72 of the respective side walls 56 and 66 enabling such juxtaposition with the leaves 60 extending altitudinally upwardly relative to the platform 52 of the tray 50. At the same time, the respective end walls 58 of the platform 52 are straddled by the corresponding side walls 66 of the leaves 60. Upon placement of the leaves 60 in the folded position, the side walls 56 and 66 and the end walls 58 extend along the side walls 44 of the casing 42, the end walls 68 extend along the top 48 of the casing 42 and, of course, the platform 52 extends along the bottom 46, so that the tray 50 grasps the casing 42 and holds the casing 42 firmly in place around the element 40 enveloped within the casing 42.

With the tray 50 thus folded around the casing 42, the casing 42, the tray 50 and the encased element 40 are inserted into the inner receptacle 14. Such insertion is facilitated by the slight outward taper of the side walls 16 from the bottom 18 toward the top 22. Each leaf 60 further includes a pair of opposite wedge-shaped ramps 76, located at laterally opposite sides of the web 64, the ramps 76 projecting from the webs 64 so as to confront and engage the corresponding side walls 16. By virtue of the wedging action of the ramps 76, the tray 50 is folded securely around the casing 42, and the assembled tray 50 and casing 42 are held firmly within the interior of the inner receptacle 14. The cover 24 of the inner receptacle 14 then is secured in place to seal the casing 42 and the tray 50 within the inner receptacle 14. The inner receptacle 14 may then be inserted into the outer receptacle 12 and the cover 34 secured in place to seal the outer receptacle 12. Thus, it can be seen that the completed package 10 is sturdy and holds the prosthetic implant element 40 securely in place within a double-sealed enclosure. The element 40 is cushioned against any damage to the dimensions or finish of the element which might affect the performance of the element 40. The packaging components themselves are constructed so as to lend themselves to the maintenance of the desired sterile conditions. At the same time, the component parts of the package 10 are constructed economically. For example, tray 50, as well as each of the receptacles 12 and 14, may be manufactured relatively inexpensively by vacuum forming techniques.

Figure 4:
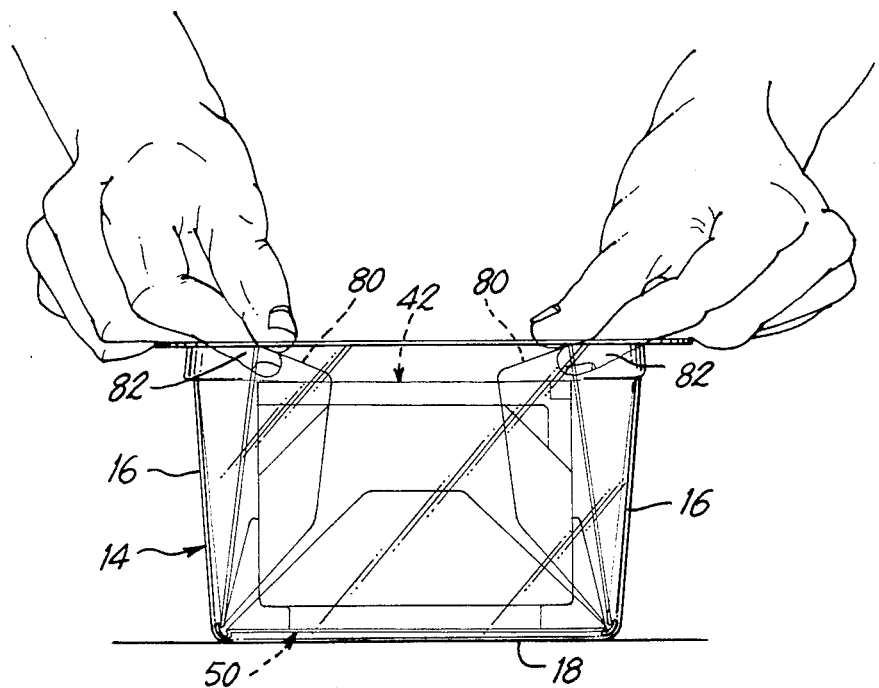
FIG. 4 is an elevational view of component parts of the package of FIG. 1.
Figure 5:
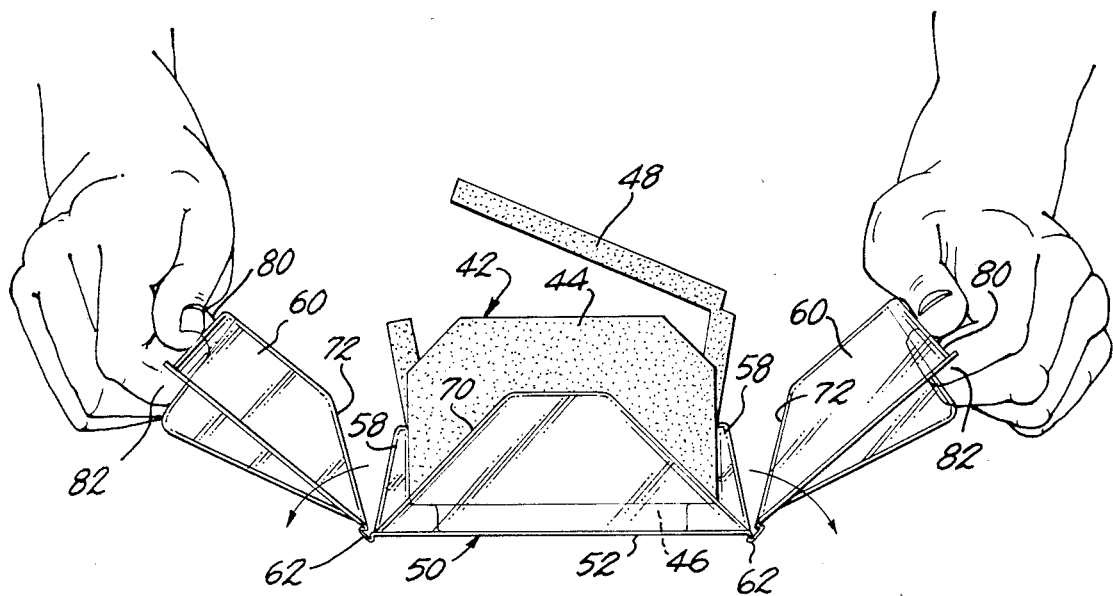
FIG. 5 is an elevational view of some of the component parts in another position.

When it is desired to present the prosthetic implant element 40 for use in an implant procedure, package 10 may be selected from stock and delivered to the vicinity of the operating room where the surgeon is to perform the implant procedure. Package 10 itself usually is stored within a cardboard box (not shown) and first will be removed from the box. Since the outer receptacle 12 has been exposed to non-sterile conditions as a result of handling during shipping, storage and the like, the next step is to remove cover 34, and discard the outer receptacle 12, so that only the relatively clean inner receptacle 14 is brought into the operating room. Once the inner receptacle 14 is in the operating room, the cover 24 is removed to expose the tray 50, as seen in FIG. 4. Tray 50 includes finger lifts 80 which project outwardly and upwardly along the uppermost edges of the leaves 60 of tray 50 when the leaves 60 are in the folded position. An operating room assistant need merely place his fingers beneath the finger lifts 80, as shown at 82 in FIG. 4, and lift the tray 50 from the receptacle 14. Once the tray 50 is withdrawn from receptacle 14, leaves 60 may be swung about the respective hinges 62, as illustrated in FIG. 5, to bring the leaves 60 to the open position, thereby releasing casing 42 and enabling the top 48 thereof to be opened for presentation of the element 40 to the surgeon for implant. In this manner the element 40 is presented directly to the surgeon without intermediate handling and the concomitant possibility of contamination. Thus, tray 50 serves the dual functions of secure packing of the element 40 and direct presentation of the element 40 for implant without contamination of the sterile conditions under which the element 40 was packaged. The tray 50 is simple in construction and may be made as a relatively inexpensive unitary structure by vacuum forming methods, as discussed above.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed as defined as follows:

1. In a package for a sterile prosthetic implant element, the package including a walled receptacle and a sealing cover for encasing the prosthetic implant element within a sterile enclosure, a tray for securing the prosthetic implant element within the enclosure for storage and shipment and facilitating removal from the enclosure and presentation of the prosthetic implant element directly to a surgeon during an implant procedure, the tray comprising:
- a platform extending longitudinally between opposite ends and laterally between opposite sides;
- a leaf hinged to the platform at each of the opposite ends of the platform, each leaf having longitudinally opposite ends and laterally opposite sides, and being movable between an open position wherein the leaves project essentially longitudinally outwardly from the ends of the platform, and a folded position wherein the leaves project essentially altitudinally from the ends of the platform; and
- confining means associated with the platform and with the leaves, the confining means arranged such that upon placement of the leaves in the folded position the tray is receivable within the receptacle, with the platform, the leaves and the confining means establishing a defined envelope within which the prosthetic implant element is confined when packaged for storage and shipment, and upon removal of the tray from the receptacle and movement of the leaves to the open position, the prosthetic implant element is presented directly to the surgeon for implant.

2. The invention of claim 1 wherein the confining means includes walls integral with the platform at the opposite sides thereof.

3. The invention of claim 1 wherein the leaves each include laterally opposite sides and the confining means includes walls integral with the leaves at the opposite sides thereof.

4. The invention of claim 3 wherein the walls project in an altitudinal direction when the leaves are in the open position.

5. The invention of claim 1 wherein the leaves each include opposite ends, each leaf being hinged to the platform at one of said opposite ends of the leaf and including a finger lift portion located adjacent the other of the opposite ends of the leaf.

6. The invention of claim 1 including means for urging the leaves toward the folded position thereof upon insertion of the tray into the receptacle.

7. The invention of claim 6 wherein said means for urging the leaves toward the folded position thereof comprises ramps located on the leaves.

8. The invention of claim 7 wherein the ramps have a wedge-shaped configuration.

9. The invention of claim 1 including a resilient pad for interposition between the confining means and the prosthetic implant element such that the resilient pad will line the envelope within which the prosthetic implant element is confined.

10. The invention of claim 9 wherein the leaves each include laterally opposite sides and the confining means includes walls integral with the leaves at the opposite sides thereof.

11. The invention of claim 10 wherein the confining means includes further walls integral with the platform at the opposite sides of the platform.

12. The invention of claim 11 wherein the tray is constructed of a unitary member of material.

* * * * *